United States Patent [19]

Worms et al.

[11] 3,962,433

[45] June 8, 1976

[54] METHOD OF TREATMENT OF CALCIUM DISORDERS USING PHOSPHONOALKANE-POLYCARBOXYLIC ACIDS

[75] Inventors: Karl-Heinz Worms, Dusseldorf-Holthausen; Christian Gloxhuber, Haan; Manfred Schmidt-Dunker, Dusseldorf; Helmut Blum, Dusseldorf-Holthausen, all of Germany

[73] Assignee: Henkel & Cie G.m.b.H., Dusseldorf, Germany

[22] Filed: Dec. 3, 1974

[21] Appl. No.: 529,040

[30] Foreign Application Priority Data
Dec. 6, 1973 Germany............................ 2360797

[52] U.S. Cl................................. 424/212; 424/204
[51] Int. Cl.²......................................... A61K 31/66
[58] Field of Search............................ 424/204, 212

[56] References Cited
UNITED STATES PATENTS

| | | | |
|---|---|---|---|
| 3,584,124 | 6/1971 | Francis | 424/204 |
| 3,683,080 | 8/1972 | Francis | 424/204 |

OTHER PUBLICATIONS

Chemical Abstracts, 80:61407m (abstracting Ger. Offen. 2,217,742, published 10–18–73.

*Primary Examiner*—Stanley J. Friedman
*Attorney, Agent, or Firm*—Hammond & Littell

[57] ABSTRACT

A method for the treatment of diseases relating to the abnormal deposition or dissolution of difficultly soluble calcium salts in the body of warm-blooded animals which consists of administering orally, parenterally or topically to said warm-blooded animals, a safe but effective amount of at least one pharmacologically acceptable phosphonoalkane-polycarboxylic acid and water-soluble salts thereof.

10 Claims, No Drawings

METHOD OF TREATMENT OF CALCIUM DISORDERS USING PHOSPHONOALKANE-POLYCARBOXYLIC ACIDS

A number of diseases are known in human and veterinary medicine which are associated primarily or partly with the abnormal deposition or dissolution of difficultly soluble calcium salts in the animal body. These diseases can be divided into two categories:
1. Abnormal depositions of difficultly soluble calcium salts, mostly calcium phosphate, cause bone malformations, pathological hardening of tissues and secretions in organs;
2. The abnormal dissolution of hard tissues causes losses of hard bone substance, which cannot be replaced or only by incompletely crystallized tissue. This dissolution is frequently accompanied by pathologically high calcium and phosphate concentrations in the plasma.

In the first category belong diseases like arthritis, neuritis, bursitis, tendinitis, and other inflammatory diseases where the deposit of calcium phosphate is enhanced in the respective body parts. Hyperparathyroidism caused by hormonal disorders can, in combination with hypercalcemia, produce a calcium deposit in many organs. Myositis ossificans (fibrodysplasia) leads to progressive ossification of the musculature, and in Bechterew's disease, a typical inflammatory disorder of the bone joint system, progressive calcification leads to an ossification of the entire vertebral system.

Particularly frequent among the diseases of the first category is arteriosclerosis, where calcificaton of the aorta and of the arteries appears as a rule in the progressive stage. Furthermore, calculi of all kinds belong here, like kidney stones, gall stones, bladder stones and sialolith (tartar). Even though these stones do not consist completely of calcium phosphate, a calcium phosphate deposit can be assumed in most cases as a nucleus.

To the second category of diseases belong hereditary hypophosphatasia as well as osteoporosis, where there is insufficient reformation of bone substance for various reasons (senile, menopausal, caused by treatment with drugs like steroids, or by diseases, like arthritis). Furthermore, this group comprises Paget's disease (Osteitis deformans) where the dissolution of normal bone substance is accompanied by reformation of soft, only slightly crystallized tissue, as well as Osteodystrophia fibrosa generalisata, a systemic disease with irregular bone disintegration.

A number of these diseases appear relatively frequently in human, as well as in veterinary medicine. A completely satisfactory therapy for these diseases has not yet been described, though controlled diets, treatment with fluorides, phosphates or condensed phosphates, with sex hormones, and particularly with the hormone calcitonin have been suggested and also used. In the last years the treatment of some of these diseases with phosphonates has been suggested, particularly 1,1-diphosphonates. In addition, U.S. Pat. No. 3,584,124 suggests treating some of these diseases with ethane-1,2-dicarboxy-1,2-diphosphonic acid and ethane-1,2-dicarboxy-1-phosphonic acid.

An object of the present invention is the development of pharmaceutical methods and pharmacological preparations which may be utilized in the treatment of the abvoe conditions.

Another object of the present invention is the development of a method for the treatment of diseases relating to the abnormal deposition or dissolution of difficultly soluble calcium salts in the body of warm-blooded animals which consists of administering orally or parenterally to said warm-blooded animals, a safe but effective amount of at least one pharmacologically acceptable phosphonoalkane-polycarboxylic acid derivative or water-soluble salts thereof.

A further object of the present invention is the development of a pharmaceutical composition consisting essentially of a minor amount of at least one pharmacologically acceptable phosphonoalkane-polycarboxylic acid derivative or water-soluble salts thereof, and a major amount of pharmacologically acceptable excipients.

These and other objects of the present invention will become more apparent as the description thereof proceeds.

The present invention relates to pharmaceutical preparations and methods for influencing the deposition and dissolution of difficultly soluble calcium salts by using certain phosphonoalkane-polycarboxylic acids or their nontoxic pharmacologically acceptable water-soluble salts as an active ingredient.

It was found that phosphonoalkane-polycarboxylic acids or their water-soluble salts are suitable for the therapeutic treatment of disorders of calcium or phosphate metabolism and of diseases caused by them. The new pharmaceutical products for influencing the deposition and dissolution of diffidultly soluble calcium salts are, therefore, characterized by the fact that they contain as an active ingredient a phosphonoalkane-polycarboxylic acid or its water-soluble salts of the formula

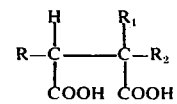
(1)

or their non-toxic pharmacologically acceptable water-soluble salts, where R is hydrogen or alkyl with 1 to 3 carbon atoms, $R_1$ is $PO_3H_2$, or

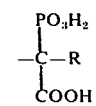

or

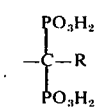

$R_2$ is hydrogen, alkyl with 1 to 3 carbon atoms, or

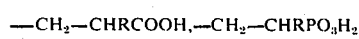

or

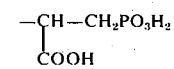

The water-soluble salts are salts of partial as well as complete neutralization. The remainder of the composition comprises an inert pharmaceutically acceptable excipient.

More particularly, therefore, the present invention relates to a method for the treatment of diseases relating to the abnormal deposition or dissolution of difficultly soluble calcium salts in the body of warm-blooded animals which consists of administering orally or parenterally to said warm-blooded animals, a safe but effective amount for said treatment of at least one pharmacologically acceptable phosphonoalkane-polycarboxylic acid derivative being a member selected from the group consisting of A. at least one phosphonoalkane-polycarboxylic acid of the formula

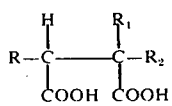

wherein R is selected from the group consisting of hydrogen and alkyl having 1 to 3 carbon atoms, wherein $R_1$ is selected from the group consisting of

and

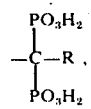

and
wherein $R_2$ is selected from the group consisting of hydrogen, alkyl having 1 to 3 carbon atoms, $-CH_2-CHRCOOH, -CH_2-CHRPO_3H_2$ and

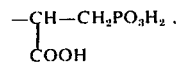

and
B. a non-toxic pharmacologically acceptable water-soluble salt of (A).

Also the present invention provides a pharmaceutical composition consisting essentially of a minor amount of at least one pharmacologically acceptable phosphonoalkane-polycarboxylic acid derivative as mentioned above, and a major amount of pharmacologically acceptable excipients.

Suitable examples of phosphonoalkane-polycarboxylic acids are listed in the following Table I. Instead of using the acids mentioned therein, the non-toxic pharmacologically acceptable water-soluble salts thereof may be utilized. Examples of these salts include the alkali metal salts, particularly the sodium salt and potassium salt, as well as the magnesium salt, and ammonium compounds as well as ammonium salts substituted by alkylol groups, for example, the alkanolamine salts, such as the mono-, di- and triethanol ammonium salts. Both the partial salts, where only a part of the acid protons are replaced by other cations, and complete salts can be used. However, the partial salts which react substantially neutral in aqueous solution (pH 5 to 9) are preferred. Mixtures of the above-mentioned salts can likewise be utilized.

TABLE I

1. Phosphono-ethane-1,2-dicarboxylic acid
2. 1-Phosphono-propane-1,2-dicarboxylic acid
3. 1-Phosphono-pentane-1,2-dicarboxylic acid
4. 2-Phosphono-propane-2,3-dicarboxylic acid
5. 2-Phosphono-pentane-1,2-dicarboxylic acid
6. 2-Phosphono-butane-2,3-dicarboxylic acid
7. 2-Phosphono-pentane-2,3-dicarboxylic acid
8. 4-Phosphono-octane-4,5-dicarboxylic acid
9. 2-Phosphono-butane-1,2,4-tricarboxylic acid
10. 2-Phosphono-pentane-1,2,4-tricarboxylic acid
11. 2-Phosphono-hexane-1,2,4-tricarboxylic acid
12. 2-Phosphono-heptane-1,2,4-tricarboxylic acid
13. 3-Phosphono-pentane-2,3,5-tricarboxylic acid
14. 3-Phosphono-heptane-1,3,4-tricarboxylic acid
15. 3-Phosphono-hexane-2,3,5-tricarboxylic acid
16. 4-Phosphono-octane-3,4,6-tricarboxylic acid
17. 5-Phosphono-nonane-4,5,7-tricarboxylic acid
18. 3-Phosphono-octane-2,3,5-tricarboxylic acid
19. 1,3-Diphosphono-butane-3,4-dicarboxylic acid
20. 2,4-Diphosphono-pentane-4,5-dicarboxylic acid
21. 3,5-Diphosphono-hexane-5,6-dicarboxylic acid
22. 2,4-Diphosphono-heptane-1,2-dicarboxylic acid
23. 1,3-Diphosphono-pentane-3,4-dicarboxylic acid
24. 1,3-Diphosphono-hexane-3,4-dicarboxylic acid
25. 2,4-Diphosphono-hexane-4,5-dicarboxylic acid
26. 3,5-Diphosphono-octane-5,6-dicarboxylic acid
27. 3,5-Diphosphono-nonane-5,6-dicarboxylic acid
28. 3,5-Diphosphono-octane,-2,3-dicarboxylic acid
29. 1,3-Diphosphono-butane-2,3,4-tricarboxylic acid
30. 1,3-Diphosphono-pentane-2,3,4-tricarboxylic acid
31. 1,3-Diphosphono-heptane-2,3,4-tricarboxylic acid
32. 1-Phosphono-propane-1,2,3-tricarboxylic acid
33. 2-Phosphono-butane-2,3,4-tricarboxylic acid
34. 3-Phosphono-pentane-1,2,3-tricarboxylic acid
35. 3-Phosphono-hexane-1,2,3-tricarboxylic acid
36. 4-Phosphono-heptane-2,3,4-tricarboxylic acid
37. 2-Phosphono-hexane-2,3,4-tricarboxylic acid
38. 4-Phosphono-nonane-4,5,6-tricarboxylic acid
39. 2-Phosphono-pentane-2,3,4-tricarboxylic acid
40. 3-Phosphono-heptane-3,4,5-tricarboxylic acid
41. 1-Phosphono-2-methyl-propane-1,2,3-tricarboxylic acid
42. 2-Phosphono-3-ethyl-butane-2,3,4-tricarboxylic acid
43. 3-Phosphono-4-methyl-pentane-3,4,5-tricarboxylic acid
44. 4-Phosphono-5-propyl-hexane-4,5,6-tricarboxylic acid
45. 2-Phosphono-3-methyl-hexane-2,3,4-tricarboxylic acid
46. 4-Phosphono-5-methyl-nonane-4,5,6-tricarboxylic acid
47. 1-Phosphono-2-methyl-pentane-1,2,3-tricarboxylic acid
48. 2-Phosphono-3-methyl-pentane-2,3,4-tricarbocylic acid
49. 3-Phosphono-4-ethyl-heptane-3,4,5-tricarboxylic acid
50. 1,1-Diphosphono-propane-2,3-dicarboxylic acid
51. 2,2-Diphosphono-butane-3,4-dicarboxylic acid
52. 3,3-Diphosphono-pentane-4,5-dicarboxylic acid 53. 3,3-Diphosphono-hexane-1,2-dicarboxylic acid
54. 2,2-Diphosphono-pentane-3,4-dicarboxylic acid
55. 4,4-Diphosphono-heptane-2,3-dicarboxylic acid
56. 1,1-Diphosphono-pentane-2,3-dicarboxylic acid
57. 3,3-Diphosphono-heptane-4,5-dicarboxylic acid
58. 1,1-Diphosphono-2-methyl-propane-2,3-dicarboxylic acid
59. 2,2-Diphosphono-3-methyl-butane-3,4-dicarboxylic acid
60. 2,2-Diphosphono-3-methyl-pentane-3,4-dicarboxylic acid
61. 3,3-Diphosphono-4-ethyl-heptane-4,5-dicarboxylic acid
62. 2,2-Diphosphono-3-propyl-heptane-3,4-dicarboxylic acid
63. 1-Phosphono-butane-2,3,4-tricarboxylic acid
64. 1-Phosphono-pentane-2,3,4-tricarboxylic acid
65. 1-Phosphono-3-methyl-pentane-2,3,4-tricarboxylic acid
66. 1-Phosphono-3-methyl-heptane-2,3,4-tricarboxylic acid
67. 1-Phosphono-3-propyl-hexane-2,3,4-tricarboxylic acid
68. 1-Phosphono-3-methyl-butane-2,3,4-tricarboxylic acid
69. 1-Phosphono-3-propyl-butane-2,3,4-tricarboxylic acid.

The production of the phosphonoalkane-polycarboxylic acids used according to the invention is effected according to known methods.

1-Phosphonoethane-1,2-dicarboxylic acid can be prepared by reacting maleic acid ester with diethyl phosphite in the presence of sodium ethanolate and subsequent acid saponification of the ester. 2-Phosphono-propane-2,3-dicarboxylic acid can be prepared in a similar manner, but the saponification must be preceded by a reaction with methyl chloride.

1-Phosphonopropane-1,2,3-tricarboxylic acid can be prepared by reacting maleic acid ester with phosophonoacetic acid ester in the presence of the above alcoholate and subsequent saponification of the ester produced. The preparation of 1-phosphonobutane-2,3,4-tricarboxylic acid can be effected by reacting dimethyl-phosphite with 1-butane-2,3,4-tricarboxylic acid ester in the presence of sodium ethanolate and subsequent saponification of the ester produced to yield the desired acid.

By reacting methane diphosphonic acid alkylester with maleic acid alkylester in the presence of sodium ethanolate, an ester is produced which is transformed by hydrolysis into 1,1-diphosphonopropane-2,3-dicarboxylic acid.

2-Phosphonobutane-2,3,4-tricarboxylic acid can be prepared by reacting α-diethyl phosphonopropionic acid methylester with diethyl maleate in the presence of the above alcoholate, and subsequent saponification of the ester obtained.

The preparation of 2,2-diphosphonobutane-3,4-dicarboxylic acid was effected by reacting maleic acid ester with ethane-1,1-diphosphonic acid ester in the presence of sodium ethanolate and subsequent acid saponification of the product produced.

The other phosphonoalkane polycarboxylic acids are prepared in a similar manner, particularly using citraconic acid ester instead of maleic acid ester.

The corresponding non-toxic pharmacologically acceptable water-soluble salts can be produced by complete or partial neutralization of the acids with an inorganic base such as an alkali metal hydroxide, for example, sodium hydroxide or potassium hydroxide, or ammonium hydroxide, or an alkanolamine such as mono-, di- and triethanolamine, as well as alkali metal carbonates such as sodium carbonate or potassium carbonate.

Instead of the free acid, its pharmacologically acceptable, water-soluble salts, for example, the alkali metal salts such as the sodium or potassium salts, the magnesium salts, the ammonium salts and substituted ammonium salts, such as lower alkylammonium and lower alkanolammonium salts, such as mono-, di- or triethanol-ammonium salts can also be used. For pharmaceutical applications, both the partial salts, in which only a part of the acid proton is substituted by other cations, and full salts can be used, but partial salts which react substantially neutral in aqueous solution (pH 5 to 9) are preferred.

The dosage range of the phosphonoalkane-polycarboxylic acid derivatives is variable and depends on the respective conditions, such as the type and severity of the disease, duration of the treatment, and the particular compound being utilized. Individual dosages can be from 0.05 to 500 mg per kg of the animal body weight. The preferred dose is 1 to 50 mg per kg of body weight, and can be administered several times daily by oral application. The preferred dose for oral administration is 1 to 10 mg per kg with a maximum of four times daily.

In the treatment of warm-blooded animals, the compounds can also be added to the feed, if necessary. The effect of the above-mentioned compounds and their salts is based presumably on an interaction of the compounds with the crystal surface of the calcium phosphate.

The following examples are merely illustrative of the present invention without being deemed limitative in any manner thereof, and demonstrate the effects that can be achieved with the new pharmaceutical preparations and methods of the invention.

EXAMPLE 1

Apatite crystallization delay test in vitro

The compounds utilized according to the invention are efficient in preventing abnormal calcium depositions. Their efficacy in this respect was demonstrated in vitro by their retarding the crystallization of apatite.

Supersaturated solutions of $Ca^{++}$ and $HPO_4^{--}$ ions are relatively stable, but crystallize after the addition of an apatite nuclei according to the reaction:

$$5\ Ca^{++} + 3\ HPO_4^{--} + H_2O \rightarrow Ca_5(PO_4)_3OH + 4\ H^+$$

with the release of protons. The reaction, therefore, can be readily observed by titration with a base at a constant pH.

400 ml of 0.008 molar $KH_2PO_4$ solution were mixed with 45 ml of a 0.012 molar $CaCl_2$ solution, and the clear solution was standardized with KOH to a pH of 7.4, after being brought to a temperature of 35°C. After 30 minutes during which time the pH did not change, a suspension of 100 mgm of hydroxyl apatite in 50 ml of $H_2O$ was added. The crystallization set in immediately and was followed by "pH-Stat" titration with 0.05 N KOH.

If the apatite before it was added to the supersaturated solution was treated for about 6 hours with small amounts of the phosphono compound inhibitors in the form of their substantially neutral salts, the crystallization was substantially inhibited. The reduction in the amount of the crystallization after four hours was between 80% and 95%. Even after some additional time, the values were still considerably lower than those without the addition of the inhibitors.

EXAMPLE 2

Prevention of hardening of the aorta in rats

The effectiveness of the phosphonoalkane-polycarboxylic acids used according to the present invention in preventing abnormal calcium deposits in vivo in rats can be demonstrated as follows.

This test was based on the observation that high doses of vitamin $D_3$ fed to rats cause a considerable hardening of the aorta in rats. 30 Female rats weighing 150 to 200 gm each were divided into three groups of ten animals each. They received during the test period a normal diet and tap water ad libitum. One group of 10 animals (control) received no further treatment. Another group of the animals received from the 3rd to the 7th day, 75,000 units of vitamin $D_3$ daily through a stomach sound. The third group likewise received from the 3rd day to the 7th day, 75,000 units of vitamin $D_3$ daily through a stomach sound and, in addition, likewise parenterally or orally, 10 mgm per kg of one of the phosphonoalkanecarboxylic acids from the 1st to the 10th day. After ten days the animals were sacrificed and their aortas prepared and dried for 12 hours at 105°C. After determination of the dry weight, the aortas were ashed, the residue was dissolved, and the calcium content in mg was determined by flame photometry. The phosphonoalkane-polycarboxylic acids used according to the invention, or their non-toxic pharmacologically acceptable salts, substantially reduce the vitamin $D_3$-induced hardening of the aortas and kidneys.

Characteristic values are indicated in Table II. These were obtained according to the above-described testing method with parenteral administration of 1-phosphonopropane-1,2-dicarboxylic acid in physiological solution. The dosage of phosphonoalkane-polycarboxylic acid used was 40 mg/kg daily. Table II in column 3 sets forth the results obtained according to the invention, compared with the values found in the control group of rats (column 1) and in rats treated exclusively with vitamin $D_3$ (column 2).

TABLE II

|  | 1 Control | Mg of Calcium 2 Vitamin $D_3$ | 3 Invention |
|---|---|---|---|
| Aorta | 580 ± 40 | 24,100 ± 8,500 | 950 ± 70 |
| Kidneys | 420 ± 70 | 960 ± 160 | 520 ± 90 |

Comparable results were obtained when any one of the other compounds listed in Table I were substituted for the particular 1-phosphonopropane-1,2-dicarboxylic acid utilized in Example 2. Comparable results were also obtained when a non-toxic pharmacologically acceptable water-soluble salt of an acid in Table I, such as the sodium salt, potassium salt, magnesium salt, ammonium salt, alkylol or alkyl substituted ammonium salt, such as the mono-, di- or triethanol ammonium salt, either as the partial salt or as the complete salt, were substituted for the particular acid utilized in Example 2.

For pharmaceutical purposes the compounds according to the present invention are administered to warm-blooded animals perorally or parenterally as active ingredients in customary dosage best modes compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like.

The following examples illustrate a few dosage unit compositions comprising a compound of the present invention as an active ingredient and represent the bestmodes contemplated of putting the invention into practical use.

EXAMPLE 3

Tablets

A tablet composition was compounded from the following ingredients by conventional methods:

| | |
|---|---|
| A phosphonoalkane-polycarboxylic acid in the form of the substantially neutral sodium salts, based upon Table I | 100 mg |
| Lactose | 100 mg |
| Starch | 40 mg |
| Magnesium stearate | 3 mg |

The above tablet contained an effective dosage unit composition for the treatment of diseases relating to the abnormal deposition or dissolution of difficultly soluble calcium salts in a warm-blooded animal.

EXAMPLE 4

Capsules

A capsule filler composition was compounded from the following ingredients by conventional methods:

| | |
|---|---|
| A phosphonoalkane-polycarboxylic acid in the form of the substantially neutral potassium salt, based upon Table I | 100 mg |
| Starch | 100 mg |
| Sodium lauryl sulfate | 1 mg |

The above ingredients constituted an effective dosage unit composition for the treatment of diseases relating to the abnormal deposition or dissolution of difficultly soluble calcium salts in a warm-blooded animal.

Analogous results are obtained when any other non-toxic pharmalogically acceptable water-soluble salt is substituted for the sodium salt or the potassium salt of Examples 3 or 4, either as a partial salt or as a complete salt, such as one of the other salts mentioned above. Likewise, the amount of active ingredient in these illustrative examples may be varied to achieve the dosage unit range set forth above, and the amounts and nature of the inert pharmaceutical carrier ingredients may be varied to meet particular requirements.

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. A method for the treatment of diseases relating to the abnormal deposition or dissolution of difficultly soluble calcium salts in the body of warm-blooded animals which consists of administering orally or parenterally to said warm-blooded animals, a safe but effective amount for said treatment of at least one pharmacologically acceptable phosphonoalkane-polycarboxylic acid selected from the group consisting of
   A. at least one phosphonoalkane-polycarboxylic acid of the formula

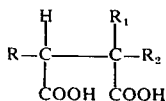

wherein R is selected from the group consisting of hydrogen and alkyl having 1 to 3 carbon atoms,
wherein $R_1$ is selected from the group consisting of

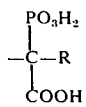

and

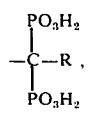

and
wherein $R_2$ is selected from the group consisting of hydrogen, alkyl having 1 to 3 carbon atoms, $-CH_2-CHRCOOH$, $-CH_2-CHRPO_3H_2$ and

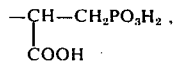

and
   B. a non-toxic pharmacologically acceptable water-soluble salt of (A).

2. The method of claim 1 wherein said phosphonoalkane-polycarboxylic acid is administered in a daily amount of from 0.05 to 500 mg/kg of the animal body weight.

3. A method for the treatment of diseases relating to the abnormal deposition or dissolution of difficultly soluble calcium salts in the body of warm-blooded animals which consists of administering orally or parenterally to said warm-blooded animals, a safe but effective amount for said treatment of at least one pharmacologically acceptable phosphonoalkane-polycarboxylic acid derivative being a member selected from the group consisting of
   A. at least one phosphonoalkane-polycarboxylic acid of the formula

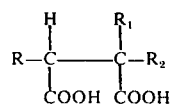

wherein R is selected from the group consisting of hydrogen and alkyl having 1 to 3 carbon atoms,
wherein $R_1$ is selected from the group consisting of

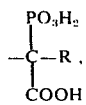

and
whrein $R_2$ is selected from the group consisting of hydrogen, alkyl having 1 to 3 carbon atoms, and $-CH_2-CHRCOOH$, and
   B. a non-toxic pharmacologically acceptable water-soluble salt of (A).

4. The method of claim 3 wherein said phosphonoalkane-polycarboxylic acid is administered in a daily amount of from 0.05 to 500 mg/kg of the animal body weight.

5. The method of claim 3 wherein R is $CH_3$, $R_1$ is $PO_3H_2$ and $R_2$ is hydrogen.

6. The method of claim 3 wherein R is hydrogen, $R_1$ is $PO_3H_2$ and $R_2$ is $-CH_2-CHRCOOH$, R again being hydrogen.

7. A method for the treatment of diseases relating to the abnormal deposition or dissolution of difficultly soluble calcium salts in the body of warm-blooded animals which consists of administering orally or parenterally to said warm-blooded animals, a safe but effective amount for said treatment of at least one pharmacologically acceptable phosphonoalkane-polycarboxylic acid derivative being a member selected from the group consisting of
   A. at least one phosphonoalkane-polycarboxylic acid of the formula

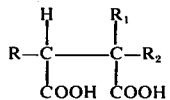

wherein R is selected from the group consisting of hydrogen and alkyl having 1 to 3 carbon atoms,
wherein $R_1$ is selected from the group consisting of $PO_3H_2$

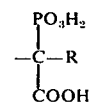

and

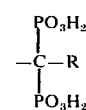

and
wherein $R_2$ is selected from the group consisting of hydrogen, alkyl having 1 to 3 carbon atoms, $-CH_2CHRCOOH$, $-CH_2-CHRPO_3H_2$ and

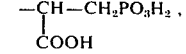

with the proviso that $R_1$ and $R_2$ are selected so that at least two $PO_3H_2$ groups are present in the molecule, and B. a non-toxic pharmacologically acceptable water-soluble salt of (A).

8. The method of claim 7 wherein said phosphonoalkane-polycarboxylic acid is administered in a daily amount of from 0.05 to 500 mg/kg of the animal body weight.

9. A pharmaceutical composition for the treatment of diseases relating to the abnormal deposition or dissolution of difficultly soluble calcium salts consisting essential of an effective amount of at least one pharmacologically acceptable phosphonoalkane-polycarboxylic acid selected from the group consisting of A. at least one phosphonoalkane-carboxylic acid of the formula

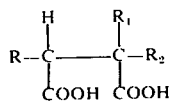

wherein R is selected from the group consisting of hydrogen and alkyl having 1 to 3 carbon atoms,
wherein $R_1$ is selected from the group consisting of $PO_{32}$

and

and wherein $R_2$ is selected from the group consisting of hydrogen, alkyl having 1 to 3 carbon atoms, $-CH_2-CHRCOOH$, $-CH_2-CHRPO_3H_2$ and

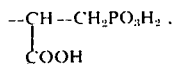

and

B. a non-toxic pharmacologically acceptable water-soluble salt of (A), and a major amount of pharmacologically acceptable excipients.

10. A pharmaceutical composition for the treatment of diseases relating to the abnormal deposition or dissolution of difficultly soluble calcium salts consisting essentially of an effective amount of at least one pharmacologically acceptable phosphonoalkane-polycarboxylic acid selected from the group consisting of A. at least one phosphonoalkane-polycarboxylic acid of the formula

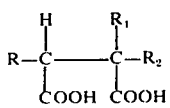

wherein R is selected from the group consisting of hydrogen and alkyl having 1 to 3 carbon atoms,
wherein $R_1$ is selected froam the group consisting of $PO_3H_2$ and

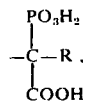

and
wherein $R_2$ is selected from the group consisting of hydrogen, alkyl having 1 to 3 carbon atoms, and $-CH_2CHRCOOH$, and B. a non-toxic pharmacologically acceptable water-soluble salt of (A), and a major amount of pharmacologically acceptable excipients.

* * * * *

UNITED STATES PATENT OFFICE
CERTIFICATE OF CORRECTION

Patent No. 3,962,433          Dated June 8, 1976

Inventor(s) Manfred Schmidt-Dunker, Helmut Blum, Karl-Heinz Worms, Christian Gloxhuber It is certified that error appears in the above-identified patent and that said Letters Patent are hereby corrected as shown below:

IN THE PATENT

| Column | Line | |
|---|---|---|
| 1 | 68 | "above" should be ---above---. |
| 3 | between lines 25 & 26 | --$PO_3H_2$,-- should be inserted. |
| 5 | 40 | "sophonacetic" should be --sphonacetic--. |
| 6 | 51 | "3$HPO_4$-" should be --3$HPO_4$--. |
| 8 | 4 | "best modes" should be --unit--. |
| 9 | between Claim 1 lines 20 & 21 | --$PO_3H_2$,-- should be inserted. |
| 10 | between lines 3 & 5 | --$PO_3H_2$ and-- should be inserted. |

UNITED STATES PATENT OFFICE
CERTIFICATE OF CORRECTION

Patent No. 3,962,433　　　　　　　　　　Dated June 8, 1976

Inventor(s) Karl-Heinz Worms et al.

It is certified that error appears in the above-identified patent and that said Letters Patent are hereby corrected as shown below:

Column 11, line 30, "$PO_{32}$" should be --$PO_3H_2$,--.

𝔖igned and 𝔖ealed this

Twenty-eighth 𝔇ay of June 1977

[SEAL]

Attest:

RUTH C. MASON　　　　　　　　　　C. MARSHALL DANN
*Attesting Officer*　　　　　　　　*Commissioner of Patents and Trademarks*